US006653516B1

(12) United States Patent
Yoshikawa et al.

(10) Patent No.: US 6,653,516 B1
(45) Date of Patent: Nov. 25, 2003

(54) PRODUCTION METHOD FOR HYDRATE AND DEVICE FOR PROCEEDING THE SAME

(75) Inventors: Kozo Yoshikawa, Takasago (JP); Yuichi Kondo, Kobe (JP); Takahiro Kimura, Kobe (JP); Tetsuro Fujimoto, Takasago (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 0 days.

(21) Appl. No.: 09/524,753

(22) Filed: Mar. 14, 2000

(30) Foreign Application Priority Data

Mar. 15, 1999 (JP) .......................................... 11-069291
Mar. 15, 1999 (JP) .......................................... 11-069294

(51) Int. Cl.[7] ................................................ C07C 9/00
(52) U.S. Cl. ......................... 585/15; 422/198; 422/199; 422/200; 422/201; 422/203; 422/205; 422/224; 422/225; 422/231; 422/234
(58) Field of Search ........................... 585/15; 422/198, 422/199, 200, 201, 203, 205, 224, 225, 231, 234

(56) References Cited

U.S. PATENT DOCUMENTS 3,510,266 A * 5/1970 Midler ....................... 422/128
5,536,893 A 7/1996 Gudmundsson

FOREIGN PATENT DOCUMENTS

| | | | |
|---|---|---|---|
| RU | 2088641 | 8/1997 | |
| WO | WO 93/01153 | 1/1993 | |
| WO | WO94/00713 | 1/1994 | |
| WO | WO 9634226 A1 * | 10/1996 | ........... F17C/11/00 |
| WO | WO98/19101 | 5/1998 | |
| WO | WO99/19282 | 4/1999 | |

* cited by examiner

*Primary Examiner*—Jerry D. Johnson
*Assistant Examiner*—Basia Ridley
(74) *Attorney, Agent, or Firm*—Oblon, Spivak, McClelland, Maier & Neustadt, P.C.

(57) ABSTRACT

A method for producing hydrate includes supplying hydrate producing substance in a gas state into an aqueous phase in a hydrate producing vessel, thereby providing the hydrate producing vessel having a gaseous phase including the hydrate producing substance and the aqueous phase, and spraying water including methane dissolved therein into the gaseous phase containing the hydrate producing substance in the hydrate producing vessel, thereby reacting the water and the hydrate producing substance to produce hydrate.

6 Claims, 9 Drawing Sheets

PRODUCTION METHOD FOR HYDRATE AND DEVICE FOR PROCEEDING THE SAME

BACKGROUND OF THE INVENTION

1. Field of the Invention

The present invention is related to a production method in which highly concentrated hydrate is produced efficiently by reacting hydrate producing substance, such as methane with water, and a device which is suitable for carrying out the same.

This application is based on Japanese Patent Applications Nos. Hei 11-69291 and Hei 11-69294, the contents of which are incorporated herein by reference.

2. Description of the Related Art

It is well known that a large amount of natural gas components, such as methane etc. are presented as hydrates under the ground of cold districts. The hydrates are existed stably at low temperatures and high pressures; therefore, they are anticipated to be natural gas sources for the next generation. In particular, a hydrate comprising methane (below simply denotes methane hydrate) is one kind of clathrate compound in which a methane molecule is situated into a cluster comprising water molecules stereoscopically positioned. The distance between methane molecules in the hydrate clusters is shorter than the distance between methane molecules in a gas cylinder under high pressure. That is, the methane molecules in a hydrate state are situated closely. Therefore, it is anticipated that to storage and transport methane in a methane hydrate state. In addition, the reaction between methane and water has a reversible equilibrium, and generates a large amount of hydration heat. Therefore, applications of a methane hydrate for a heat storage material, refrigerator, heat pump, etc. are currently being investigated.

As described above, many applications of the methane hydrate are anticipated, and therefore an investigation of synthesizing methane hydrate with a high efficiently is carried out, in addition to depending on the natural resources. However, in general, the pressure at which the methane hydrate is stabilized at 15° C. is 100 kg/cm$^2$ or greater. That is, methane hydrate is stabilized under conditions of low temperatures and high pressure; therefore, it is difficult to handle the methane hydrate. The handling the methane hydrate under such conditions is difficult. In order to solve the problem, many kinds of stabilizers for shifting the formation equilibrium conditions of the methane hydrate to the conditions of high temperatures and low pressures, have been investigated. As a result, it has been discovered that for example, aliphatic amines such as isobuthyl amine, isopropyl amine, etc. (Japanese Patent Publication, Second Publication No. Sho 53-1508 (Koukoku)), 1-3-dioxysolane, cyclobutanone, tetrahydrofuran, cyclopentanone, acetone, etc. (Seiichi Yokoi and others, Nippon Kagaku Bulletin, 1993 (4), page 378 to 394) are useful as stabilizers.

The production method in which hydrate is produced by spraying water into a gaseous phase of ethane which is one of the hydrate producing substance, thereby contacting ethane and water with a large contact area, has been suggested (INTERNATIONAL CONFERENCE ON NATURAL GAS HYDRATES (JUN. 2–6, 1996 TOULOUSE FRANCE).

In general, a device shown in FIG. 9, for example, has been used to produce methane hydrate using the above-mentioned production method. In FIG. 9, the synthesis device for methane hydrate comprises a pressure vessel 150 equipped with an aqueous phase injection pipe 151, a methane gas injection pipe 152, an outlet 153, and an agitator 154. The pressure vessel 150 is put into a thermostatic bath 155. Furthermore, the synthesis device comprises thermometers for measuring temperatures T1 and T2 in a gaseous phase and an aqueous phase in the pressure vessel 150, a pressure meter for measuring pressure P in the pressure vessel 150, an instrument for measuring a rotational frequency R of the agitator 154, and a thermometer for measuring temperature T3 in the thermostatic bath 155.

In order to synthesize the methane hydrate using the synthesis device, for example, an air in the pressure vessel 150 is expelled by introducing a methane gas in the pressure vessel 150 from the methane gas injection pipe 152. Then, an aqueous solution containing the stabilizer having a desired concentration is introduced into the pressure vessel 150 from the aqueous phase injection pipe 151 as an aqueous phase. The temperature of the aqueous phase in the pressure vessel 150 is set at the desired temperature by the thermostatic bath 155. Methane gas is introduced into the pressure vessel 150 from the methane gas injection pipe 152 while stirring with the agitator 154 until the pressure in the pressure vessel 150 reaches a desired pressure. When the stirring is carried out keeping these conditions, a hydration reaction occurs, and the pressure P in the pressure vessel 150 decreases. In addition, the temperature T2 of the aqueous phase rises due to a heat of hydration. The synthesis device is left alone until the temperatures T1 and T2 of the gaseous phase and the aqueous phase which are enclosed by the thermostatic bath 155 are substantially equal, while the pressure P in the pressure vessel 150 is adjusted by exhausting a part of the methane gas from the outlet 153, if necessary. Then, methane hydrate having a formation equilibrium pressure P at the temperature T2 can be obtained.

However, the conventional methane hydrate production method using the production device shown in FIG. 9 has following problems. The reaction between methane and water is carried out due to an absorption of methane gas into the aqueous phase at a gas-liquid interface. As shown in FIG. 10, the density of the methane hydrate MH produced by the reaction is smaller than the density of water (the theoretical density of methane hydrate is 0.915 g/cm$^2$). Therefore, the methane hydrate MH comes near the surface of a liquid phase (aqueous phase) L, and forms a methane hydrate layer. The adsorption of methane M at the surface between a gaseous phase G and a liquid phase is prevented by the methane hydrate layer. In addition, the viscosity of the liquid phase L increases, depending on the production degree of the methane hydrate, and the stirring effect of the liquid phase L is insufficient. Consequently, it is difficult to produce the methane hydrate having a high concentration.

In addition, the concentration of the methane hydrate in the liquid phase L increases, depending on an amount of methane gas injected from the methane gas injection pipe 152. However, the ratio of water to the methane gas, which remains in the liquid phase L decreases, while the reaction is carried out. Then, the reaction reaches an equilibrium, and the hydration reaction does not proceeded. Therefore, from this point of view, it is also difficult to produce methane hydrate having a high concentration.

Furthermore, the period from the introduction of the aqueous solution into the pressure vessel 150 to the end of hydration reaction between the aqueous solution and the methane gas, is long. Namely, a long period to fix the temperature T2 of the aqueous solution at a desired temperature by the thermostatic bath 155, is necessary. Therefore, the production efficiency of the methane hydrate is low.

Water particles contact ethane with a large contact area in the production method in which water is sprayed in an ethane gaseous phase. However, there is the possibility that the produced hydrate adhering the surface on especially large water particle like an epidermis. The water particles enclosed by the, hydrate does not react with the ethane gas. From this point of view, there is still room for improvement of the production efficiency of the hydrate. In addition much time is necessary to reduce the temperature of the sprayed water into the reaction vessel to the temperature required to produce the hydrate. Therefore, there is also still room for improvement of the production efficiency of the hydrate.

Therefore, an object of the present invention is to provide a production method for hydrates in which the hydrate producing substance and water are reacted efficiently and highly concentrated hydrate is produced in a highly efficient and short period, and a production device suitable for promoting the production method.

SUMMARY OF THE INVENTION

According to a first aspect of the present invention, the present invention provide a production method for hydrate in which water and hydrate producing substance are reacted in a hydrate producing vessel comprising the steps of:

spraying water into a gaseous phase containing the hydrate producing substance in the hydrate producing vessel, thereby hydration reacting between water and the hydrate producing substance; and supplying the hydrate producing substance in a gas state into an aqueous phase in the hydrate producing vessel.

According to the production method of the present invention, the temperature of the aqueous phase in the vessel is set in a range of 1 to 5° C., for example, and the temperature of the aqueous phase is maintained in following processes. When the temperature of the aqueous phase is fixed at the required temperature, the hydrate producing substance, such as methane in a gas state is introduced into the aqueous phase from a lower part of the aqueous phase. Thereby, at least a part of the hydrate producing substance is absorbed by the aqueous phase from a gas-liquid interface, reacts with water, and changes to hydrate. The density of the hydrate produced by the reaction is smaller than the density of water. Therefore, the hydrate comes near the surface of the aqueous phase, accumulates at the surface of the aqueous phase, and forms a hydrate layer. Then, only hydrate layer is recovered. In this reaction system, the bubbles containing the hydrate producing substance rise continuously in the aqueous phase: therefore, the surface of the bubbles is not covered with hydrate having a highly density, and always contact water. As a result, the reaction between water and the hydrate producing substance is carried out efficiently. When the production method of the present invention is carried out stably and continuously, highly concentrated hydrate can be produced continuously and efficiently.

Non-reacted hydrate producing substance in a gas state which is not absorbed by the aqueous phase is effused from the top surface of the aqueous phase, accumulates at the top of the vessel, and form a gaseous phase. When water is sprayed into the gaseous phase, water and the hydrate producing substance in a gas state are contacted and hydrate is produced rapidly. In other words, the surface area per fixed volume of water increases by spraying. Then, the contact area between water and methane increases remarkably. Thereby, the formation rate of hydrate increases. The produced hydrate falls to the top surface of the aqueous phase, and derived, namely collected. Moreover, it is possible to recover water from the aqueous phase in the vessel and spray.

Furthermore, more rapid production of hydrate can be achieved by spraying supercooling water prepared in advance into the gaseous phase. That is, when supercooling water contacts the hydrate producing substance, the temperature of the hydrate production reaction system is reduced. Then, in order to maintain the thermal equilibrium of the reaction system, that is, to rise the temperature of the reaction system, the reaction between water and methane is promoted. In other words, in order to generate hydration heat, the hydration reaction rapidly occurs. Then, the methane hydrate can be rapidly produced. The supercooling water may be obtained by recovering water from the aqueous phase and cooling. Moreover, the same effect which is obtained by using supercooling water, can be obtained by increasing the pressure of hydrate production reaction system.

According to a second aspect of the present invention, the present invention provide a device for producing hydrate comprising:

a hydrate producing vessel, a conditions adjusting device for adjusting the temperature and the pressure in the hydrate producing vessel to suitable conditions for producing hydrate, a water supplying device for supplying water in the hydrate producing vessel and producing an aqueous phase, a hydrate producing substance supplying device for supplying hydrate producing substance into the aqueous phase in the hydrate producing vessel and forming a gaseous phase containing hydrate producing substance, a spraying device for spraying water into the gaseous phase in the hydrate producing vessel, and a hydrate recovery device for recovering produced hydrate from the aqueous phase.

According to the device of the present invention, it is possible to carrying out the first production method easily and certainly. In addition, a spray nozzle or an ultrasonic vibration body can be used as the spraying device. The ultrasonic vibration body accumulates water and makes water particles fine by ultrasonic vibration. For example, the ultrasonic vibration body is preferably in a plate shape. When the ultrasonic vibration body is used as the spraying device, water particles can be divided more finely and uniformly. Then rapid production of hydrates can be achieved.

According to a third aspect of the present invention, the present invention provide a production method for hydrate in which water and hydrate producing substance are reacted in a hydrate producing vessel comprising the steps of:

ultrasonic vibrating a gaseous phase containing the hydrate producing substance and/or an aqueous phase in the hydrate producing vessel, thereby separating a produced hydrate coating adhering a surface on a water particle from the water particle; and spraying water into a gaseous phase containing hydrate producing substance in the hydrate producing vessel, thereby hydration reacting with water and the hydrate producing substance.

According to the production method of the present invention, the surface area per fixed volume of water increases by spraying. Then, the contact area between water and the hydrate producing substance increases remarkably. Thereby, it is possible to increase the formation rate of hydrate.

Furthermore, there is the possibility that the produced hydrate adhering the surface on especially large water particle like an epidermis or a coating by the conventional production method. However, the epidermises (coating) comprising hydrate adhering the surface on especially large water particle are eliminated by vibrating the gaseous phase and/or the aqueous phase in the production method of the present invention. Then, water particle which is not already enclosed by hydrate can react with hydrate producing substance. Therefore, rapid production of hydrate can be achieved by the production method of the present invention.

According to a fourth aspect of the present invention, the present invention provide a device for producing hydrate comprising:

- a hydrate producing vessel,
- a conditions adjusting device for adjusting the temperature and the pressure in the hydrate producing vessel to suitable conditions for producing hydrates,
- a hydrate producing substance supplying device for supplying hydrate producing substance into the hydrate producing vessel and forming a gaseous phase containing hydrate producing substance,
- a spraying device for spraying water into the gaseous phase,
- a hydrate coating eliminating device for ultrasonic vibrating the gaseous phase and/or the aqueous phase in the hydrate producing vessel,
- a hydrate recovery device for recovery hydrate from the aqueous phase.

According to the device of the present invention, it is possible to carrying out the production method easily and certainly. In addition, an ultrasonic vibration generator provided with the outer wall of the vessel or the inner wall of the vessel, can be used as the hydrate eliminating device. Furthermore, the shape of the ultrasonic vibration generator may be a plate shape suitable for providing to the vessel wall or a net shape in which water particles can pass through.

DESCRIPTION OF THE PREFERRED EMBODIMENTS

Below, the production method for hydrate and the device for producing hydrate are explained referring to Figures. Moreover, in the following explanation, methane is used as a hydrate producing substance. That is, the production method for methane hydrate and the device for producing methane hydrate are explained below, for convenience. Of course, the hydrate producing substance used in the present invention are not specifically limited to methane, but include ethane, propane, butane, Krypton, Xenon, carbon dioxide, etc.

Figure 2A:
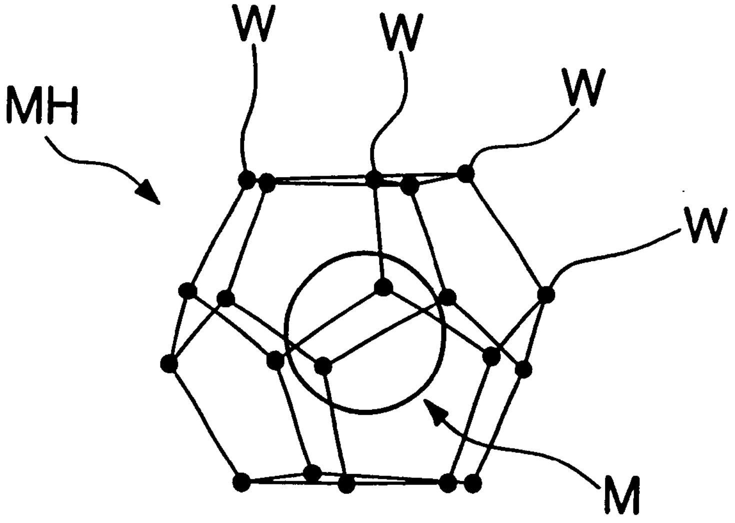
FIGS. 2A and 2B show molecular structures of hydrates.
Figure 2B:
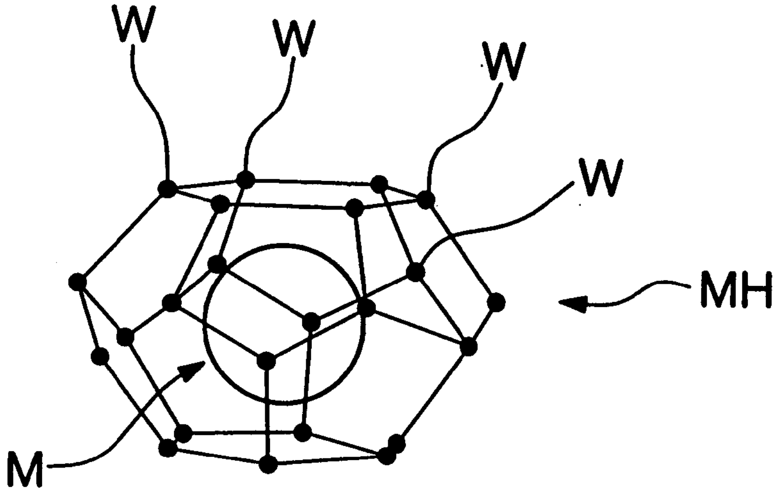

As shown in FIGS. 2A and 2B, methane hydrate MH is one kind of clathrate hydrate producing substance in which a methane molecule M is situated in a cluster comprising water molecules W stereoscopically positioned so as to form a dodecahedron and tetradecahedron. For example, methane hydrate MN is produced as shown in the reaction formula below. Moreover, when the methane hydrate MH is decomposed, approximately 0.9 of water and 170 of methane gas are generated per 1 unit of methane hydrate in volume in a normal state.

$$CH_4+5.7H_2O \rightarrow CH_4 \cdot 5.7H_2O+\text{hydration heat}$$

Figure 1:
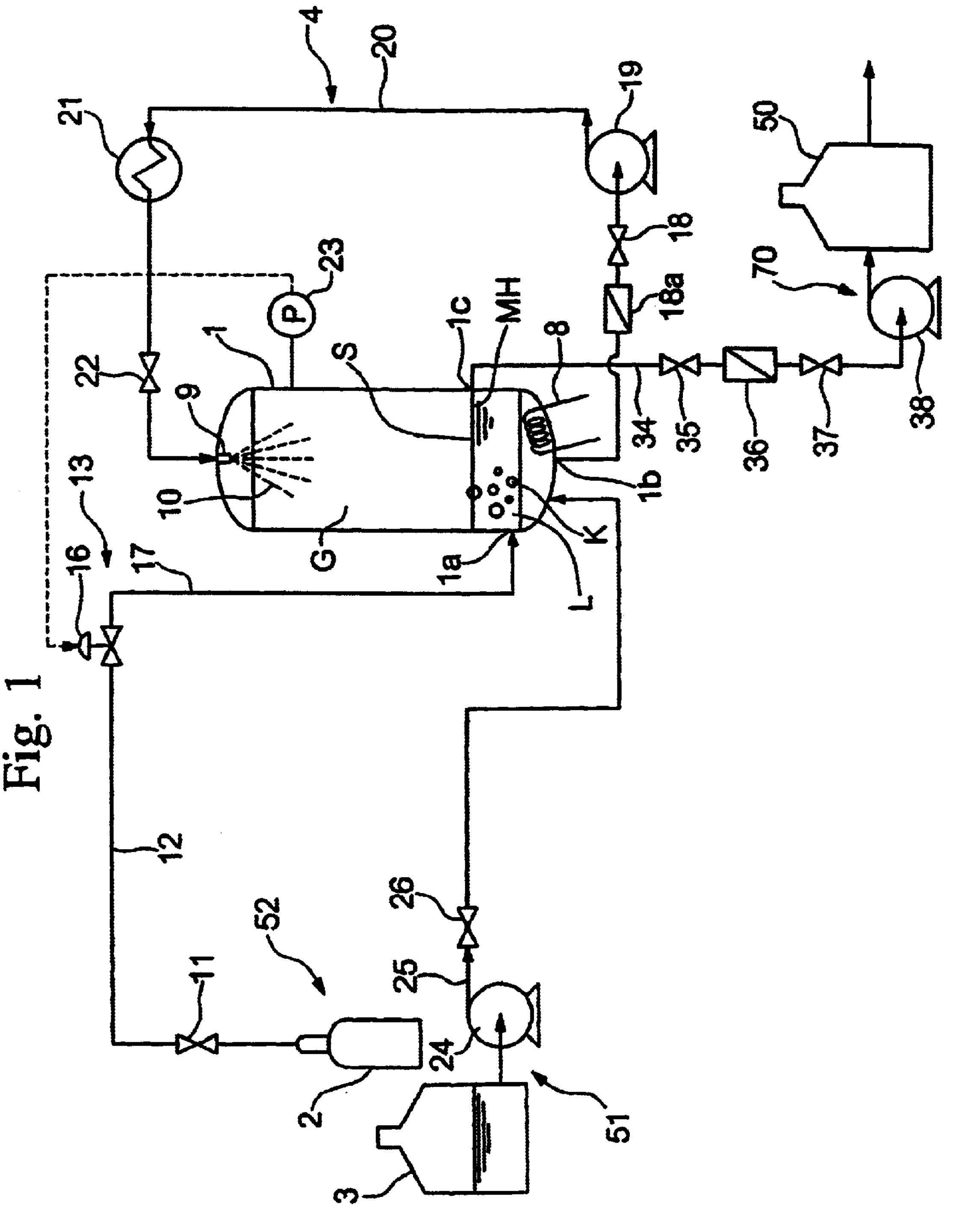
FIG. 1 is a diagram showing a first embodiment of a device according to the present invention.

FIG. 1 is a diagram showing a first embodiment of a device according to the present invention. In FIG. 1, reference numeral 1 denotes a sealed hydrate producing vessel (reaction vessel). The cooling coil 8 is provided within the hydrate producing vessel 1 as a cooling device (temperature adjusting means). The temperature of the aqueous phase L which is explained below in the hydrate producing vessel 1 can be reduced and maintained at the required temperatures for producing methane hydrate, for example 1 to 5LC by the cooling coil 8. In this embodiment, the temperature of the aqueous phase L is maintained at 1° C. When methane hydrate MH is produced, hydration heat is generated. However, in order to produce methane hydrate MH, the reaction conditions must be adjusted to low temperatures and high pressures. Therefore, it is preferable to provide the cooling coil 8 in the vessel 1 and maintain the temperature of the aqueous phase L at a reduced level. In this embodiment, the cooling coil 8 is used as a cooling device, as explained above. However, the present embodiment is not limited absolutely to the cooling coil 8. For example, the same effect can be obtained by enclosing the vessel 1 by a cooling jacket, supplying brine to the cooling jacket from a brine tank, and circulating the brine. In addition, a radiator may be provided in the vessel 1. Furthermore, these components may be combined.

In FIG. 1 reference numeral 3 denotes a water storage tank. The aqueous phase (liquid phase) L is formed in the vessel 1 by supplying water into the hydrate producing vessel 1 from the water storage tank 3 through the pipe 25. The pipe 25 is provided with the water supplying pump 24 and the valve 26, and thereby the surface S of the aqueous phase L is maintained at a fixed level. Moreover, the water storage tank 3, the water supplying pump 24, the pipe 25, etc. comprise a water supplying device 51.

The methane inlet 1*a* is provided at the lower side wall of the vessel 1. Methane gas (hydrate producing substance) is supplied to the methane inlet 1*a* through the pipe 12 from the methane tank 2 as a methane gas resource. The pipe 12 is provided with the normal valve 11 and the flow control valve (control component) 16. The opening degree of a flow control valve 16 which is explained below, is adjusted by the pressure meter 23 which measures the pressure of the gaseous phase G containing methane gas in the vessel 1. It is always possible to maintain the pressure of the gaseous phase G at the required pressure for producing methane hydrate (40 atm in this embodiment) by adding methane gas in the vessel 1 using these components. Moreover, the methane tank 2, the pipe 12, etc. comprise a methane supplying device (the hydrate producing substance supplying means) 52. The pressure meter 23 and the flow control valve 16 comprise an adjusting device 13 of the pressure in the vessel 1.

The water outlet 1*b* for deriving water is provided with the bottom of the hydrate producing vessel 1. Water derived from the water outlet 1*b* is supercooled, and then returns into the vessel 1. Specifically, the water outlet 1*b* and the spray nozzle 9 provided at the top of the vessel 1 are connected by the pipe 20. The pipe 20 is provided, sequentially from the water outlet 1*b* to the spray nozzle 9, with a valve 18, a water circulating pump 19, a heat exchanger (cooler) 21, and a valve 22. The water drained by the water circulating pump 19 is supercooled by the heat exchanger 21, and supplied as a mist 10 into the gaseous phase G (methane atmosphere) in the vessel 1 by the spray nozzle 9.

The supercooling water is the water maintained in a liquid phase when it is cooled less than its melting point. When the supercooling water contacts methane, the temperature of the hydrate production reaction system is reduced, as shown by the arrow X in FIG. 3. Then, in order to maintain the thermal equilibrium of the reaction system, the reaction between water and methane is promoted to rise the temperature of the reaction system. In other words, in order to generate hydration heat, the hydration reaction rapidly occurs, and the methane hydrate can be produced rapidly. Moreover, the same effect can be obtained by increasing the pressure of the hydrate production reaction system. In other words, when the pressure of the hydrate production reaction system increases, as shown by the arrow Y in FIG. 3, the reaction between water and methane is promoted to decrease the pressure of the reaction system to maintain the pressure equilibrium of the reaction system. That is, in order to decrease the pressure of the reaction system, the hydration reaction rapidly occurs, and the methane hydrate can be produced rapidly.

Figure 3:
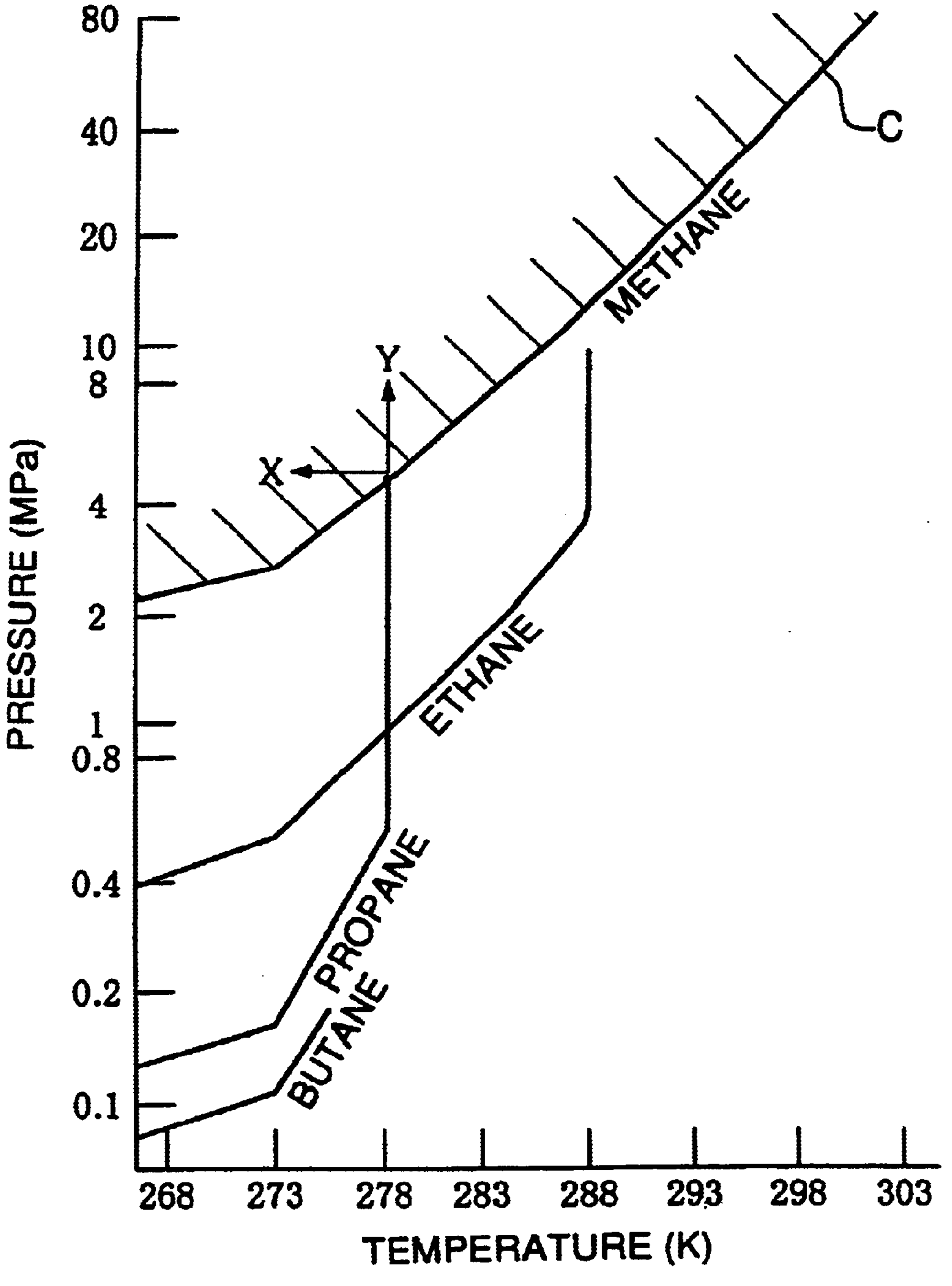
FIG. 3 shows the temperature and the pressure of the reaction system when hydrates production reaction is equilibrium.

Moreover, in FIG. 3, the line C denotes the production equilibrium line showing the relationship between the temperature and the pressure of the reaction system when hydration reaction between water and methane is in an equilibrium state. The upper area (the area indicated by oblique lines) from the production equilibrium line C is the hydrate production area. For reference, the production equilibrium lines for ethane, propane, and butane are also indicated in FIG. 3.

As the heat exchanger (cooler) 21, for example, the poly-pipe type heat exchanger having an excellent thermal conduction efficiency, the coil type heat exchanger having a simple structure, the plate type heat exchanger having an excellent thermal conduction efficiency and easy maintenance, can be used.

Moreover, a water circulating pump 19, a pipe 20, a heat exchanger 21, etc. comprise a supercooling water circulating device (water circulating means) 4.

Figure 4A:
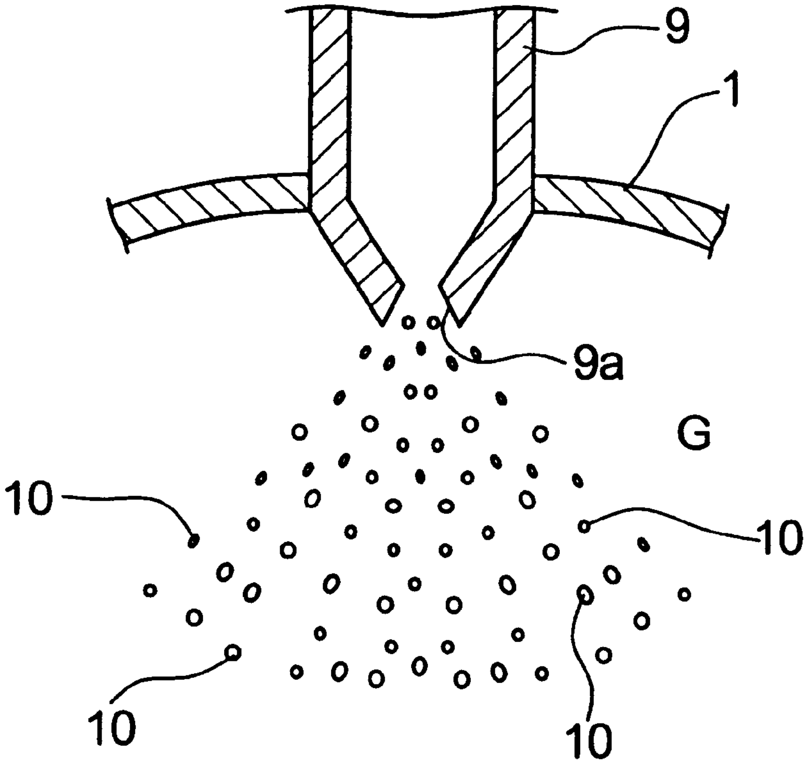
FIG. 4A is an enlarged view showing the spraying device shown in FIG. 1.

As shown in FIG. 4A, the spray nozzle (spraying means) 9 is provided at the top of the vessel 1 so as to face down. The spray nozzle 9 sprays, from the nozzle opening 9*a*, water particles 10 having an average outside diameter of scores of micrometers (an average outside diameter as small as possible is ideal) in the gaseous phase G. When water is sprayed and a large number of water particles are produced in the gaseous phase G the surface area per fixed volume of water increases remarkably. That is, the contact area for water with gaseous phase G increases remarkably. When water recovered from the bottom of the vessel 1 is sprayed into the vessel 1 by the spray nozzle 9, it is important to prevent jamming of the spray nozzle 9 due to foreign material. In order to prevent jamming, as shown in FIG. 1, it is preferable to provide in the pipe 20 a filter 18*a* for catching foreign material such as hydrate, thereby removing the certainty the foreign material from the water derived from the vessel 1.

The liquid layer outlet 1*c* is provided on the vessel 1 corresponding to the vicinity of the surface S of the aqueous phase L. The liquid layer outlet 1*c* and the hydrate recovery tank 50 are connected by the pipe 34. The pipe 34 is provided, sequentially from the liquid layer outlet 1*c*, with the valve 35, the filter 36, valve 37, deriving pump 38. Methane hydrate MH having a lower density than the density of water floating on the surface S passes through the pipe 34. Then, the foreign material contaminated in methane hydrate MH are removed by the filter 36. After that, methane hydrate MH is collected in the hydrate recovery tank 50. When the hydrate recovery device 70 is used, methane hydrate MH can be collected together with water. The mixture containing methane hydrate MH and water is in a slurry state, therefore, handling the methane hydrate MH is easy.

Below, the functions of the produced device, that is, the production method for hydrate is explained.

Air in the hydrate producing vessel 1 is displaced with methane gas. Then, water is introduced from the water storage tank 3 into the vessel 1 before the surface S of water reaches a position higher than the liquid layer outlet 1*c*, thereby the aqueous phase L is produced. The aqueous phase L may contain stabilizers, if necessary. Then, the aqueous phase L in the vessel 1 is cooled to the required temperature, for example 1° C., by the cooling coil 8. The temperature of the aqueous phase L is maintained in following processes.

Once the temperature of the aqueous phase L has stabilized at the required temperature, methane is introduced continuously from the methane inlet 1*a* as bubbles K from the methane tank 2 through the pipe 17, as shown in FIG. 1. When methane in a gas state is supplied into the aqueous phase L, at least a part of the methane is absorbed byto the aqueous phase L from the gas-liquid interface, reacts with water, and changes to methane hydrate. Namely, a hydration reaction occurs. Methane hydrate MH produced by the hydration reaction has a lower density than the density of water; therefore, it rises within the aqueous phase L, floats on the surface S of the aqueous phase L, and produces a methane hydrate layer. The methane hydrate layer is taken out of the vessel 1 from the liquid layer outlet 1*c* by the deriving pump 38, and collected in the methane hydrate recovery tank 50. Methane hydrate MH is collected with water; therefore, it is in a slurry state. When the methane hydrate layer is derived from the liquid layer outlet 1*c*, the surface S of the aqueous phase L goes down. In order to maintain the surface S of the aqueous phase L at a fixed level, fresh water is supplied from the water storage tank 3 into the vessel 1 through the water supplying pump 24. In addition, when methane hydrate MH is produced within the vessel 1, methane gas changes to methane hydrate which is in a solid state, and the pressure in the vessel 1 decreases. However, in order to produce methane hydrate rapidly, the pressure in the vessel 1 should be maintained at a high level. Therefore, in order to prevent the pressure in the vessel 1 decreasing due to the production of methane hydrate MH, the pressure in the vessel 1 is continuously measured by the pressure meter 23. Then, the degree of opening of the flow control valve 16 is adjusted continuously based on the pressure in the vessel 1. Thereby, a required amount of methane gas is supplied into the vessel 1, the pressure in the vessel 1 is maintained at a fixed high value. More rapid production of hydrate can be achieved by these processes.

Non-reacted methane gas which is not absorbed by the aqueous phase L is effused from the surface S of the aqueous phase L, accumulates in the vessel 1, and forms the gaseous phase G. Water which is derived from the bottom of the vessel 1 and supercooled by the heat exchanger 21 is sprayed into the vessel by the spray nozzle 9. Then, the contact area per fixed volume of water particles 10 to methane gas increases remarkably. In addition, the temperature of the hydration reaction system is reduced by using supercooling water. Thereby, the hydration reaction between water and methane occurs rapidly, and methane hydrate is produced rapidly. The produced hydrate falls to the top surface S of the aqueous phase L, and is derived and collected in the same manner explained above.

Moreover, when methane hydrate MH is produced in the vessel 1, a large hydration heat is generated. However, in order to rapidly produce methane hydrate MH, the temperature in the vessel 1 should be maintained at a reduced level. When supercooling water particles 10 are sprayed into the vessel 1, hydration heat is removed efficiently. From this point of view, use of supercooling water is preferable.

When the hydrate production vessel 1 is of a large scale, there is the possibility that the water at the bottom of the vessel 1 will be supercooled. Therefore, water at the bottom of the vessel 1 may be sprayed into the vessel 1 from the spray nozzle 9, without cooling.

According to this embodiment, the bubbles K containing methane gas rise within the aqueous phase L, while they are not enclosed with methane hydrate which has a large density. Namely, the bubbles K can always make contact with fresh water molecules. The hydration reaction between methane and water is promoted. When the production method of this embodiment is carried out stably and continuously, highly concentrated methane hydrate can be collected continuously and efficiently in the methane hydrate recovery tank 50.

When the water particles 10 sprayed from the spray nozzle 9 have a large diameter, methane hydrate formed on the surface of the water particles 10 form a methane hydrate coating and prevents contact between methane and water. Then the inside water enclosed with the methane hydrate coating cannot reacts with methane. The adhesion of methane hydrate on the surface of the water particles 10 can be decreased by spraying water together with gas from the spray nozzle 9, that is, using ejecting gas. When the water is sprayed together with ejecting gas, water particles 10 are divided so that the average particle diameter is approximately 10 $\mu$m. Inert gases which do not react with water and the hydrate producing substance, such as methane can be used as the gas. The number of the spray nozzles 9 is not limited to only one. A plurality of the spray nozzles 9 can be provided.

Figure 4B:
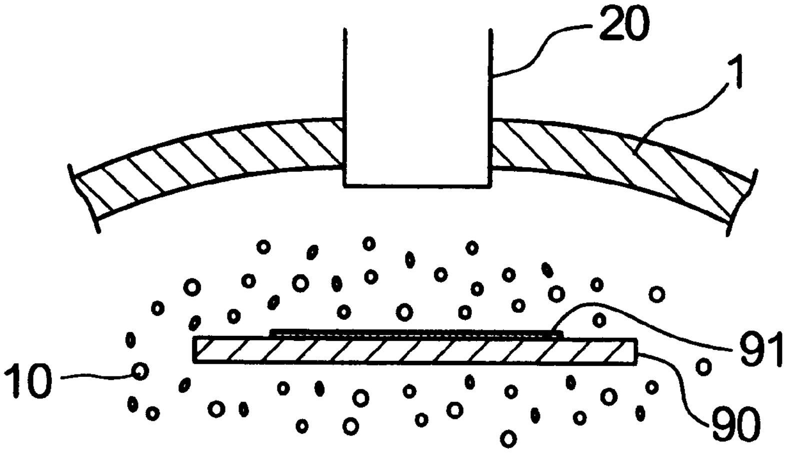
FIG. 4B shows another spraying device.

As another method for dividing water particles 10 so that the average particle diameter is approximately 10 $\mu$m, a method using an ultrasonic vibration plate 90 can be demonstrated. As shown in FIG. 4B, an ultrasonic vibration plate 90 is provided toward the top of the vessel 1. A water film 91 is formed on the ultrasonic vibration plate 90 by supplying supercooling water by the pipe 20. Then water particles 10 are emitted from the water film 91 by ultrasonic vibration. According to this method, there are no bad adverse effects due to the ejection of gases, compared with the above method in which ejecting gas is used. In addition, the particle diameter of the water particles 10 is more uniform than the water particles 1 produced by the above method. Moreover, for example, the ultrasonic vibration body 90 is preferably in a plate shape.

In general, the reaction between methane and water is carried out at a pressure of 40 atm or greater when the temperature is 1° C. Therefore, a high pressure vessel having a withstanding pressure of 40 atm or greater is necessary for the hydrate production vessel 1. When it is necessary to carry out the hydration reaction under conditions in which the pressures is lower than 40 atm, it is suitable to add stabilizers to the aqueous phase L. The stabilizers for carrying out the hydration reaction under lower pressure are not specifically limited to but includes aliphatic amines such as isobuthyl amine and isopropyl amine; alicyclic ethers such as 1,3-dioxofuran, tetrahydrofuran, furan; alicyclic ketones such as cyclobutane, cyclopentane; and aliphatic ketones such as acetone. These stabilizers contain a hydrocarbon group and a polar group in their molecule. The hydrocarbon group attracts a methane molecule, and the polar group attracts a water molecule. Thereby, it is believed that the molecular distance between methane and water decreases, and the hydration reaction promotes. For example, when the stabilizer contains aliphatic amines, the hydration reaction can be carried out at 10° C. and 20 kg/cm$^2$G. When the stabilizer contains tetrahydrofuran, the hydration reaction can be carried out at 10° C., and 10 kg/cm$^2$G or less. It is preferable to use these stabilizers in a range of 0.1 to 10 mol per 1000 g of pure water.

The reaction temperature is preferably as low as possible, when there is concern that the methane hydrate production reaction will generate hydration heat. However, when the temperature is below the freezing point of the aqueous phase L, the aqueous phase L freezes, and it is difficult for methane to react. Therefore, the reaction temperature is preferably in a range of from the freezing point of the aqueous phase L to as low a temperature as possible. For example, the temperature of the aqueous phase L is preferably in a range of 1~5° C. The solubility of methane in water can be increased and the pressure of the reaction system can be decreased by adjusting the temperature of the aqueous phase L in a range of 1~5° C. As explained above, the reaction between water and methane generates hydration heat. Therefore, when the hydration reaction is carried out in the hydrate producing vessel 1, the temperature in the vessel increases. It is preferable to always maintain the temperature of the reaction system at the required temperature range, that is, maintain the temperature in the vessel 1 to the required temperature range.

Below, another embodiment of the present invention is explained referring to the Figures.

Figure 5:
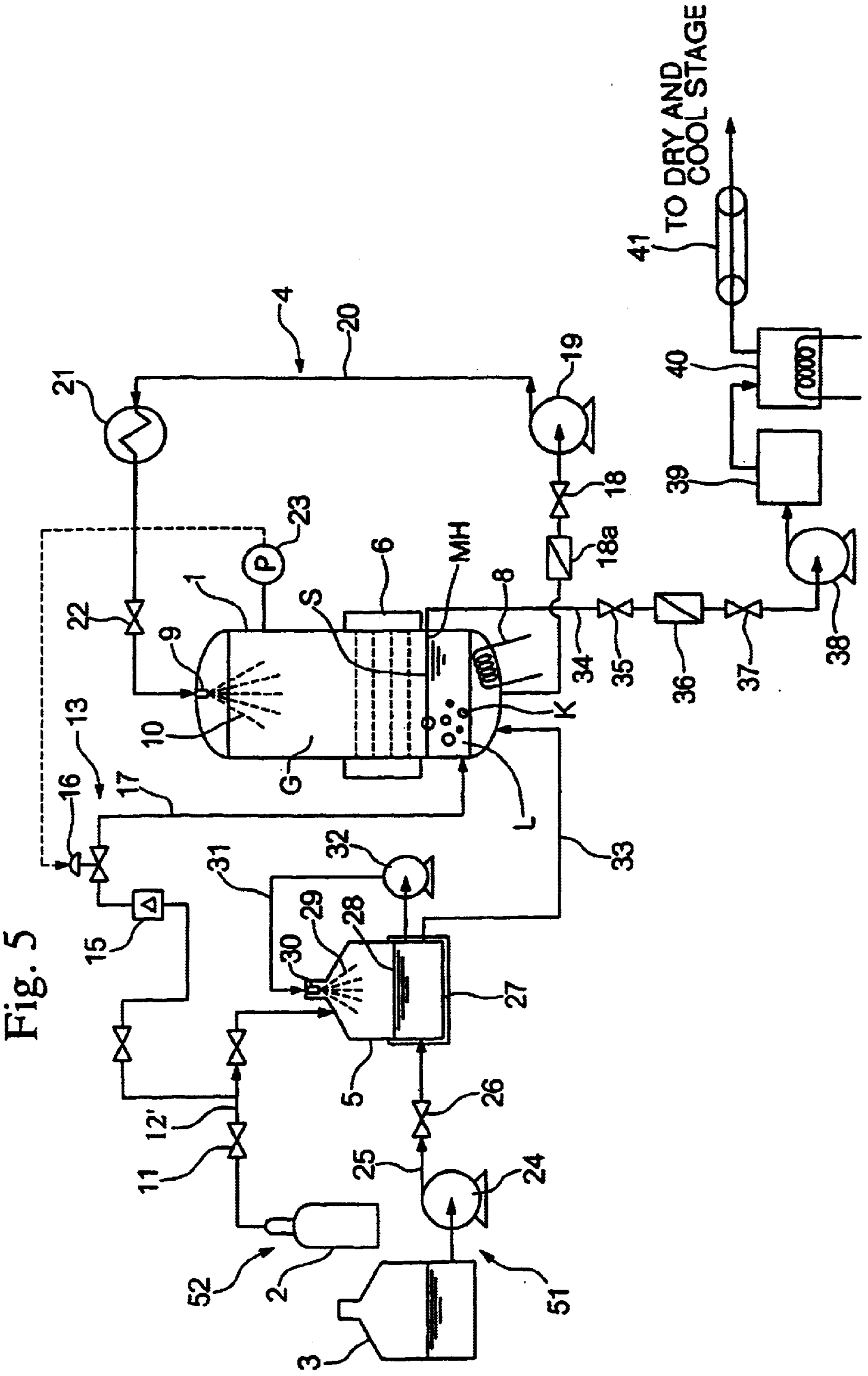
FIG. 5 is a diagram showing a second embodiment of a device according to the present invention.

FIG. 5 shows a second embodiment of a device according to the present invention. Moreover, in order to make the difference between the devices shown in FIGS. 1 and 5 clear, the components shown in FIG. 5 which are the same as the components shown in FIG. 1 have the same reference numerals as shown in FIG. 1. Thereby, an explanation for those same components is omitted in this embodiment.

In FIG. 5, reference numeral 5 denotes the tank containing water saturated with methane. Methane gas is supplied to the tank 5 from the methane tank 2 through the pipe 12'. Water is also supplied to the tank 5 from the water storage tank 3 by the water supplying pump 24. Thereby, water 28 saturated with methane is produced in the tank 5. The water 28 saturated with methane is supplied to the hydrate producing vessel 1 through the pipe 33. In order to prepare the water 28 saturated with methane, it is preferable to increase the contact area between the water and methane. Therefore, methane gas is preferably introduced into the liquid phase in the tank 5 containing water saturated with methane.

As explained above, methane hydrate has a structure in which a methane molecule is situated in a cluster comprising water molecules. When water molecules are previously positioned so as to form a cluster, methane hydrate is produced more rapidly. This effect is called a “memory effect”. The process in which water is saturated with methane in advance is effective to obtain the memory effects. In order to produce methane hydrate rapidly, water saturated with methane is most preferable. However, the memory effect can be better obtained by water in which methane is dissolved, compared with mere water. Therefore, the water used in this embodiment is not limited to water saturated with methane, it includes water in which methane is dissolved.

The tank 5 containing water saturated with methane is provided with a jacket 27 as the cooling means. Brine supplied from the brine tank (not shown in FIG. 5) by the brine pump (not shown in FIG. 5) circulates in the jacket 27. Thereby, the water 28 saturated with methane in the tank 5 is maintained under conditions in which the temperature is approximately 5° C. and the pressure is approximately 40 atm. In this embodiment, the jacket 27 is used as the temperature adjustment means. However, a temperature adjustment means other than the jacket 27 can be used this embodiment. For example, the same effect obtained by the jacket 27 can be obtained by using a tank 5 comprising a double-wall or a multiple-wall and circulating brine in a space between the walls. In addition, the same effect can be obtained by providing a cooling coil or radiator in the tank 5. Furthermore, these apparatuses may be combined.

In order to bring the dissolving level of methane in water to the saturated level, it is preferable to frequently bring the water and methane into contact by spraying water 28 in which methane is dissolved into the gaseous phase containing methane. That is, it is preferable to sending the water 28 in which methane is dissolved to the top of the tank 5 by the pump 32 and the pipe 31, and spray it by the nozzle 30 into the methane gas, thereby forming a water mist 29 in the methane gas. Moreover, the water 28 in which methane is dissolved is stirred by these processes.

Figure 6A:
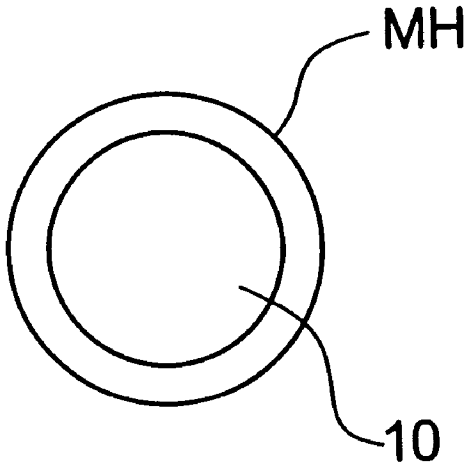
FIG. 6A shows water particle enclosed by methane hydrate.
Figure 6B:
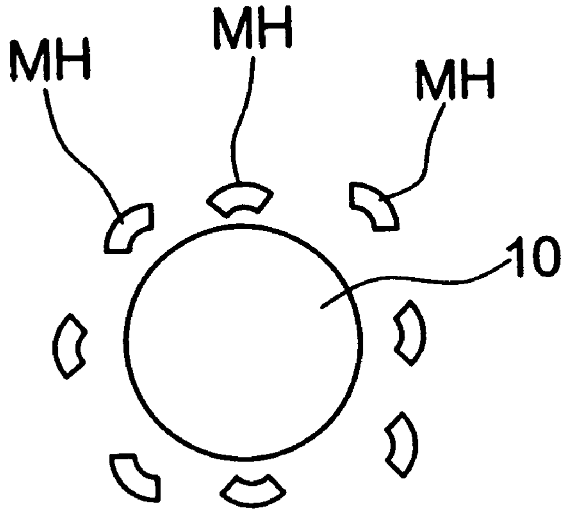
FIG. 6B shows water particle eliminated methane hydrate adhering the surface of water particle.

When methane hydrate is produced by spraying water (water saturated with methane) into the gaseous phase containing hydrate producing substance, there is the possibility that the produced hydrate will adhere to the surface of especially large water particle like an epidermis or a coating, as shown in FIG. 6A. These water particles 10 enclosed by methane hydrate MH do not produce methane hydrate. Therefore, the elimination of the coating comprising methane hydrate MH is necessary. In order to eliminate the coating comprising methane hydrate MH, an ultrasonic vibration generator 6 is provided with the hydrate producing vessel 1 so as to vibrate the gaseous phase G in the vessel 1, for example, as the methane hydrate coating breakage means in this embodiment. Thereby, as shown in FIG. 6B, the methane hydrate coating which encloses the water particle 10 in the gaseous phase G is broken, and then the methane hydrate coating separates from the water particles 10. As a result, the water particle can react with methane again. Therefore, according to this embodiment, the rapid production of methane hydrate can be achieved.

Figure 7A:
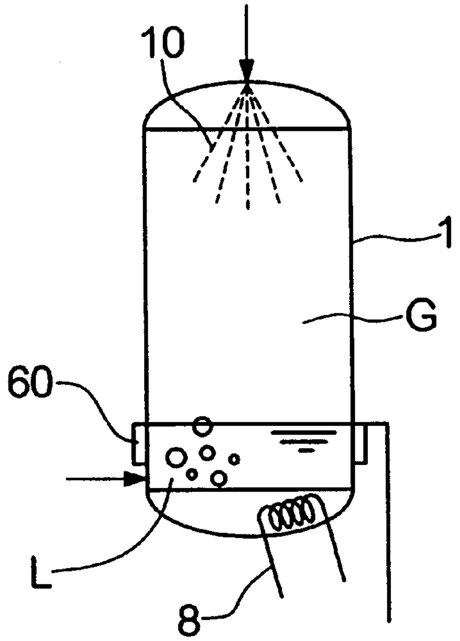
FIG. 7A shows a hydrate eliminating device provided with a device according to the present invention.
Figure 7B:
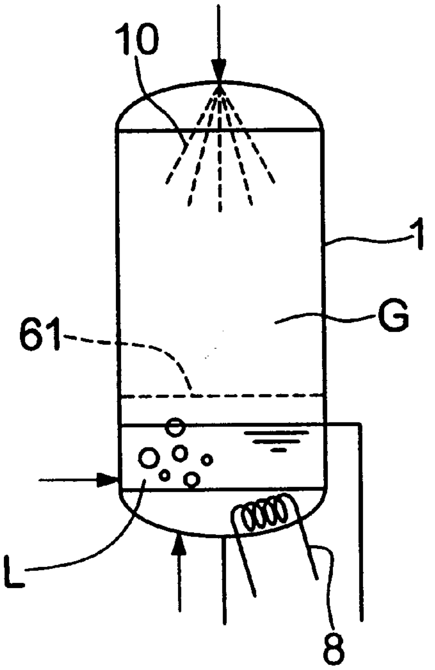
FIG. 7B shows another hydrate eliminating device provided with a device according to the present invention.

In this embodiment, the ultrasonic vibration generator 6 is provided so as to vibrate only the gaseous phase 6, as shown in FIG. 5. That is, the ultrasonic vibration generator 6 is provided with the hydrate producing vessel 1 at a position within the gaseous phase G. However, it is possible to provide the ultrasonic vibration generator 60 so as to vibrate only the aqueous phase L, as shown in FIG. 7A. That is, the ultrasonic vibration generator 60 is provided with the hydrate producing vessel 1 at a position within the aqueous phase L. In addition, it is also possible to provide the ultrasonic vibration generator 6 with the vessel 1 so as to vibrate both the gaseous phase G and the aqueous phase L. That is, it is possible to provide one ultrasonic vibration generator 6 which vibrates both the gaseous phase G and the aqueous phase L or two ultrasonic vibration generators 6, one which vibrates the gaseous phase G and one which vibrates the aqueous phase L. Furthermore, it is also possible to provide an ultrasonic vibration net 61 on the inside wall of the vessel 1 so as to be positioned substantially even level with the gaseous phase G. When the ultrasonic vibration net 61 vibrates, the methane hydrate coating adhered to the water particles 10 passing through the ultrasonic vibration net 61 is broken. Moreover, the ultrasonic vibration net 61 is not limited to a net shape, it includes an ultrasonic vibration body comprising a plurality of ultrasonic vibration lines each of which is parallel. In general, the cost for vibrating the gaseous phase G is smaller than the cost for vibrating the aqueous phase L. Therefore, it is more preferable to provide the ultrasonic vibration generator 6 in the gaseous phase G.

An integrated flowmeter 15 is provided on the pipe just before the flow controlling valve 16 which is one component comprising the methane supplying means 52. The total volume of methane supplied into the hydrate producing vessel 1 is measured by the integrated flowmeter 15. Thereby, the total amount of methane hydrate produced can be calculated easily and exactly. Moreover, the water particles to which methane hydrate is adhered are sometimes contain in the methane hydrate. Therefore, it is impossible to grasp the exact amount of methane hydrate produced by simply measuring the amount of produced methane hydrate.

In this embodiment, the pipe 34 is provided, sequentially from the liquid layer outlet 1*c*, with a valve 35, a filter 36, a valve 37, and a recovery pump 38 from the liquid layer outlet 1*c*, similar to those shown in FIG. 1. However, a centrifugal separator 39, a decompression container 40 in which the pressure decreases under adiabatic expansion, a conveyer 41, etc. are provided sequentially within the pipe downstream from the recovery pump 38 in this embodiment.

Figure 8:
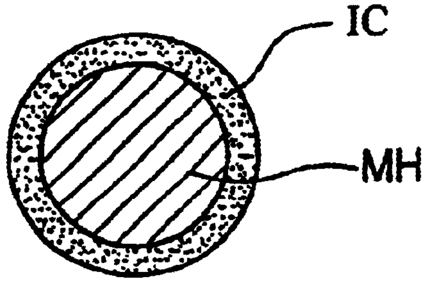
FIG. 8 shows hydrates enclosed by an iced coating.
Figure 9:
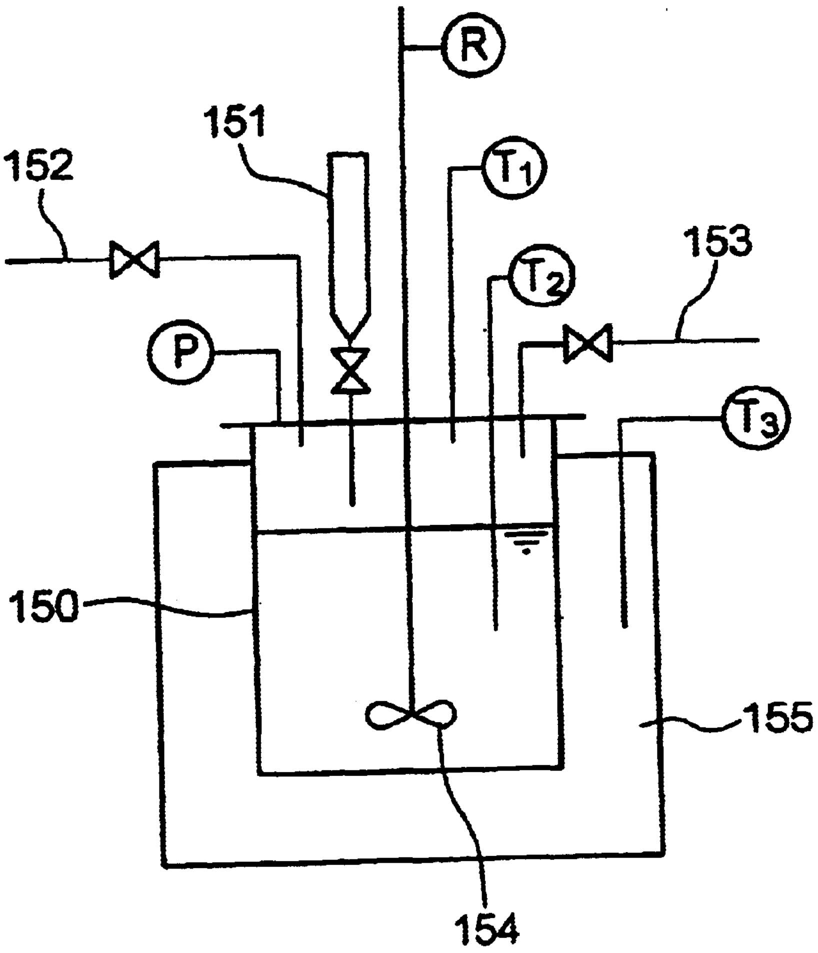
Fig. 9 BACKGROUND ART
FIG. 9 is a diagram showing a conventional device for hydrates.
Figure 10:
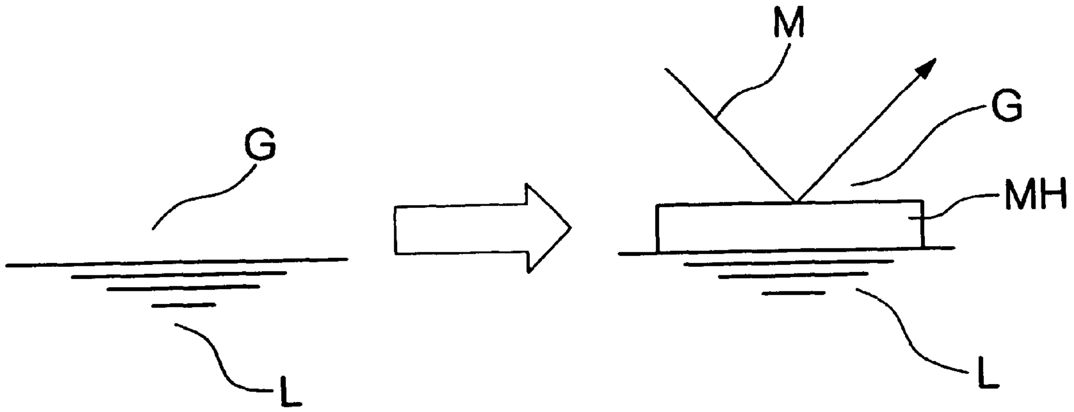
FIG. 10 is a diagram for explaining a problem to be solved.

Methane hydrate MH recovered from the hydrate producing vessel 1 is introduced into the centrifugal separator 39 by the recovery pump 38. In the centrifugal separator 39, most of the moisture contained in the methane hydrate MH is removed, and the methane hydrate MH in a slurry state is prepared. The pressure in the centrifugal separator 39 is approximately 40 atm which is substantially equal to the pressure into the hydrate producing vessel 1. Then, the prepared methane hydrate in a slurry state is sent to the decompression container 40. Methane hydrate is stabilized by adiabatically expanding the inside of the decompression container 40 to several atm, and thereby forming an ice coating IC on the surface of the methane hydrate MH as shown in FIG. 8 while the temperature and the pressure in the decompression container 40 is maintained at the required conditions for producing methane hydrate. The produced methane hydrate is sent to a drying process and a cooling process by the conveyer 41, if necessary.

In these embodiments, water is recovered from the bottom of the hydrate producing vessel 1, supercooled, and sprayed into the gaseous phase G in the hydrate producing vessel 1. However, the present invention is not limited to these embodiments. Water may be sprayed without supercooling. In addition, water or supercooling water supplied from another system may be sprayed into the gaseous phase in the hydrate producing vessel 1.

What is claimed is:

1. A method for producing hydrate, comprising the steps of:

supplying hydrate producing substance in a gas state into an aqueous phase in a hydrate producing vessel, thereby providing the hydrate producing vessel having a gaseous phase including the hydrate producing substance and the aqueous phase; and spraying water including methane dissolved therein into the gaseous phase containing the hydrate producing substance in the hydrate producing vessel, thereby reacting the water and the hydrate producing substance to produce hydrate.

2. A method according to claim 1, wherein the water is derived from a bottom portion of the aqueous phase in the hydrate producing vessel and sprayed into the gaseous phase.

3. A method according to claim 1, wherein the water comprises supercooling water prepared in advance.

4. A method according to claim 1, wherein the water is derived from the aqueous phase in the hydrate producing vessel, supercooled, and sprayed into the gaseous phase.

5. A method for producing hydrate, comprising the steps of:

supplying hydrate producing substance in a gas state into an aqueous phase in a hydrate producing vessel, thereby providing the hydrate producing vessel having a gaseous phase including the hydrate producing substance and the aqueous phase;

spraying water including methane dissolved therein into the gaseous phase in the hydrate producing vessel, thereby reacting the water and the hydrate producing substance to produce hydrate; and vibrating at least the gaseous phase containing the hydrate producing substance in the hydrate producing vessel with ultrasonic vibration, thereby separating a produced hydrate adhering to a surface of a water particle from the water particle.

6. A method for producing hydrate, comprising the steps of:

supplying hydrate producing substance in a gas state into an aqueous phase in a hydrate producing vessel, thereby providing the hydrate producing vessel having a gaseous phase including the hydrate producing substance and the aqueous phase;

spraying water including methane dissolved therein into the gaseous phase in the hydrate producing vessel, thereby reacting the water and the hydrate producing substance to produce hydrate; and vibrating at least one of the gaseous phase containing the hydrate producing substance and the aqueous phase in the hydrate producing vessel with ultrasonic vibration, thereby separating a produced hydrate adhering to a surface of a water particle from the water particle.

* * * * *